(12) United States Patent
Peterson

(10) Patent No.: US 6,477,906 B1
(45) Date of Patent: Nov. 12, 2002

(54) AUTOMATIC MULTI-SORBENT TUBE AIR SAMPLER

(75) Inventor: Roger Peterson, Old Ocean, TX (US)

(73) Assignee: Roger Peterson Family Limited, Sweeny, TX (US)

(*) Notice: Subject to any disclaimer, the term of this patent is extended or adjusted under 35 U.S.C. 154(b) by 0 days.

(21) Appl. No.: 09/515,554

(22) Filed: Feb. 29, 2000

Related U.S. Application Data

(60) Provisional application No. 60/122,376, filed on Mar. 2, 1999.

(51) Int. Cl.$^7$ .................................................. G01N 1/24
(52) U.S. Cl. ................ 73/863.21; 73/31.02; 73/863.31; 73/863.72; 73/864.34
(58) Field of Search ......................... 73/863.21, 863.72, 73/863.31, 864.34, 863.12, 31.02, 863.71, 863.73, 31.01

(56) References Cited

U.S. PATENT DOCUMENTS

| | | | | |
|---|---|---|---|---|
| 3,953,152 A | * | 4/1976 | Sipin .................... | 73/863.21 X |
| 4,030,369 A | * | 6/1977 | Etheridge ................ | 73/863.33 |
| 4,576,054 A | * | 3/1986 | Lalin .................... | 73/863.21 X |
| 4,584,887 A | * | 4/1986 | Galen ................... | 73/863.72 X |
| 4,612,019 A | * | 9/1986 | Langhorst ................ | 95/52 |
| 4,786,472 A | * | 11/1988 | McConnell et al. | 73/863.21 X |
| 5,000,052 A | | 3/1991 | Sipin ........................ | 73/863.03 |
| 5,047,073 A | * | 9/1991 | Stetter et al. ................ | 95/8 |
| 5,512,168 A | * | 4/1996 | Fetner et al. ............ | 210/198.2 |
| 5,547,497 A | | 8/1996 | Klemp et al. .................. | 96/104 |
| 5,585,575 A | * | 12/1996 | Corrigan et al. ..... | 73/863.21 X |
| 5,621,180 A | * | 4/1997 | Simon et al. ......... | 73/863.01 X |
| 5,646,357 A | * | 7/1997 | Ogden et al. ............ | 73/863.31 |
| 5,783,756 A | * | 7/1998 | Xiong et al. ......... | 73/863.33 X |
| 6,321,609 B1 | * | 11/2001 | Mengel et al. ........... | 73/863.21 |

* cited by examiner

Primary Examiner—Thomas P. Noland
(74) Attorney, Agent, or Firm—Moser, Patterson & Sheridan, L.L.P.

(57) ABSTRACT

A sampling system for capturing samples of trace elements in ambient air comprises a multi-port valve coupled to a plurality of sorbent tubes. Each tube is connected to the multi-port valve by means of pairs of the valve ports. The multi-port valve is constructed and operated in a predetermined sequence to create a flow path through the multi-port valve. The flow path directs an air sample to only one connected sorbent tube at a given time and for a given time interval.

24 Claims, 4 Drawing Sheets

AUTOMATIC MULTI-SORBENT TUBE AIR SAMPLER

This application claims the benefit of Provisional U.S. patent Application Ser. No. 60/122,376 filed Mar. 2, 1999.

FIELD OF THE INVENTION

The present invention relates generally to the field of apparatus and methods for gathering and analyzing samples of gas, and, more particularly, to systems for automatically collecting a plurality of air samples for subsequent analysis at a remote location.

BACKGROUND OF THE INVENTION

There are many applications in which it is desirable to collect gas samples from a particular environment, and to subsequently analyze these samples for certain constituents, and in particular for minor or trace constituents. A typical application for this technology is the United States manned space flight program where archival air samples are collected from the interior of a spacecraft, and subsequently analyzed for constituents of the samples at a ground based location. Analysis of these samples has been a key component of the assessment of spacecraft air quality for crew health purposes. Periodic analysis at predetermined time intervals, such as intervals during a flight, is also important in the overall air quality assessment program.

In using air sampling techniques in ground-based applications, sampling is typically linked to eight-hour time intervals to correctly assess an employee's exposure during a typical "work day". In using air-sampling techniques in space flight applications, the "work day" of a spacecraft crew is typically twenty-four hours. Although experience has shown that spacecraft air quality regarding major constituents such as oxygen and nitrogen is stable over long periods such as months, substantial changes in trace constituents or contaminants can occur over a twenty four hour period as the crew engages in different activities such as exercise and experiments. Therefore, a twenty-four hour integrated sample of spacecraft air would most accurately represent crew exposure to possible air contaminants.

Under normal circumstances, contaminant concentrations during shorter sampling periods might be unduly biased by one or more crew activities during the sample time, and longer sampling time periods would tend to average or "flatten" contaminant fluctuations. A twenty-four hour sample collects a sufficient quantity of certain constituents that are present in very low concentrations so that such constituents might not otherwise be detected. Furthermore, automatic sampling is desirable. Conditions can be encountered, however, when shorter sampling periods are desirable, and when manual initiation of the sampling is required.

In effectively sampling air for human use, means are required which trap volatile organic contaminants, but not major constituents such as nitrogen, oxygen, carbon dioxide, and water. In space flight applications, sampling means which conserve power are also desirable since spacecraft power is limited. Prior art systems employ a solid sorbent air sampler unit (SSAS) to monitor spacecraft cabin air. The SSAS consists of a plurality of tubes containing a sorbent and into which sampled air is directed by mean of a valving system. The SSAS is a manually activated device that requires a crew member to manipulate a valve to collect an air sample in a tube containing sorbent material and then record the time of this sample session.

Manual operation is subject to human error or mechanical and has resulted in samples which are unusable. For example, batteries which operate an SSAS system may be exhausted during a mission, resulting in unusable samples. The sampling acquisition valve may not be switched to the next sample tube in a timely manner resulting in an unusable sample due to a sample "overload" of the sorbent in the tube. Sample collection times may go unrecorded, or be recorded improperly, or recorded illegibly, once again resulting in an unusable sample. The SSAS sample pump used to draw samples into the sample tube may malfunction, but notice of the malfunction may not be provided, resulting in questionable samples in all tubes rendering the samples unusable.

In addition to the sampling problems and lack of automation discussed above, various flow rate orifices are subject to clogging. Changing tube sorbents is extremely difficult because sample tubes must be removed from the sampling device. The overall configuration of the system is not ideally suited for this procedure.

Other air sampling systems have been used on board spacecraft. These systems, like the SSAS, suffer from certain shortcomings. For example, glass-lined sample collection tubes present a breakage hazard. Such tubes require disassembly after sampling so that they can be cleaned in order not to contaminate subsequent sampling cycles. Such systems may also suffer cross contamination of samples due to multi-port valve design, and o-ring contamination of drawn sample gases.

In view of these prior art methods and apparatus, an object of the present invention is to provide a gas sampling system which can be used to collect a number of samples of gas for subsequent analysis.

Another object of the invention is to provide a system which employs sorbents in sample tubes, and the sorbents are sensitive to trace contaminants but not the major constituents of air.

Yet another object of the present invention is to provide sampling tubes which can be adjusted in size to accommodate varying amounts of sorbent, which are silica-lined metal and therefore have inert surfaces, yet do not present a breakage hazard, and from which samples can be drawn for analysis without physically removing the sample tube from the sample apparatus.

Another object of the invention is to provide a fully programmable sampling sequence which can draw samples at predetermined times and for predetermined intervals, with manual override capabilities which can be used to draw a sample at the discretion of an operator.

Still another object of the invention is to provide a system which can be cleaned, perform sampling, and then be desorbed without disassembling the device. This insures sample integrity and prevents any contamination from the analytical processes.

Another object of the present invention is to provide a sampling system which uses minimal electrical power thereby extending the life of batteries operating the system for long sampling periods.

Although the invention is directed toward sampling air in spacecraft, it should be understood that the invention can be used for other applications such as sampling air in the vicinity of hazardous materials manufacturing facilities, sampling air in contained environments, and the like. Other objects and applications of the invention will become apparent in the following disclosure.

SUMMARY OF THE INVENTION

The sampling system of the present invention will be referred herein to as an Automated Multi-Sorbent Tube Air Sample, or "AMTAS". The apparatus comprises a "multi-port" valve and 16 sorbent tubes. Each tube is connected to the multi-port valve by means of pairs of the valve ports. The multi-port valve is constructed and operated in a predetermined sequence to create a flow path through the multi-port valve. The flow path directs an air sample to only one connected sorbent tube at a given time and for a given time interval.

In operation, a gas sample flows from a sample source, such as air from a spacecraft cabin, through an inlet filter and intake line, into a primary inlet port of the multi-port valve, through the multi-port valve, through the sequentially connected sorbent tube, back through the multi-port valve and out through a primary outlet port, through a pump, and then through a pump exhaust. The action of the pump draws the sample into and through the connected sorbent tube.

The sequencing of the multi-port valve, the time at which flow is initiated through a given sorbent tube, and the duration of the flow through a given sorbent tube, is controlled by a processor such as a computer. The movement of the multi-port valve is controlled by an actuator cooperating with the computer, which moves the valve to one of thirty two positions, for example, under the control of the computer. Sixteen of the valve positions discretely align a given sorbent flow tube in the sample collection geometry as described above. The other sixteen valve positions are "park" positions as will be described below.

The AMTAS is capable of collecting sixteen archive samples, and the computer is preprogrammed to collect the samples at predetermined times and for predetermined intervals. The preprogrammed collection times and intervals can, however, be manually overridden by an operator such as a spacecraft crew member to obtain an "unscheduled" sample. The entire system is battery powered.

The sorbent tubes are constructed of silica-lined metal tubing and in multiple loops so that the volume of the tube can be adjusted to accommodate varying amounts of sorbent to capture particular contaminants of interest. The pump, which draws samples into and through the sorbent tubes, is operated in a pulsed mode only during sampling thereby conserving battery power. After a preset sampling time, the computer processor either switches the multi-port valve to the next sorbent tube, or moves the valve to one of the sixteen park positions.

In a park position, the valve is set between ports, thereby isolating all sorbent tubes in this position. This saves energy since the multi-port valve then needs to be turned only a fraction of an inch to align the intake and exhaust ports of the next sorbent tube when called for by the control processor. This prevents the power drain of the valve actuator having to rotate repeatedly to a single designated parking position between sampling intervals, and then returning to the next sorbent tube called for by the computer controlled sample sequence.

During the collection of samples, the AMTAS cooperates with a clock and an output device to automatically record the time of initiation and the duration of each sampling. The system also logs all other sampling operations including error messages should any system malfunction occur.

The system can also monitor any unusual event. For example, one sorbent tube may be reserved for contingency purposes. Should such a previously identified contingent event occur, an operator may slide a mode switch from AUTO to MANUAL and depress a guarded button, thereby automatically causing the control processor to rotate the multi-port valve to the specified tube and the sample collection pump to run for a predetermined time period.

Once the sampling system is returned to a facility for analysis of the collected samples, the pump is disconnected from the multi-port valve at the primary outlet port, and a source of ultra pure nitrogen is connected to this port. Each sorbent tube, as it is selected for desorption, is released from a clamp and bent downward approximately ninety degrees by means of coil spring fittings and placed into a desorption heater without removing the tube from the AMTAS. Other tubes are unaffected during this process. A clean, proofed, evacuated gas sample container (GSC) is attached to the sample inlet fitting, nitrogen is directed through the multi-port valve and through the sorbent tube being heated, back through the multi-port valve and inlet fitting and into the GSC. The sorbent tube is then removed from the heater and cooled. The multi-port valve is closed to isolate the GSC, and the GSC is removed from the system for analysis with a gas chromatograph/mass spectrometer.

After removing the sorbent sample using the carrier gas method, each sorbent tube is heated with the nitrogen flow to purify the sorbent, ready for the next sampling sequence. It is unnecessary, therefore, to disassembly to AMTAS for desorption and cleaning prior to repeated usage. The sample tubes are mounted in the system on coiled tubing "springs", which permit the sample tubes to be individually selected for heating/desorption, while the tubes remain connected into the system, and all other sample tubes remain undisturbed until selected.

Thus, in summary, it is a feature of the present invention to provide an automated sampling system in which a plurality of samples of trace elements present in ambient air are gathered under the control of a processor. It is a further feature of this invention to stage a plurality of sample tubes in minimum of space. It is a still further feature of the invention to position inlet and outlet ports of the sample tubes in adjacent ports of a multi-port valve, resulting in a looped-tube design. It is yet another feature of the invention to provide a "park" position in the automated sampling system so that an energy-saving minimum of travel is required to move the sampling system from a sample position to a position in which all sample tubes are isolated. It is still another feature of the invention to mount the sample tubes on coiled tubing springs so that a sample can be desorbed and analyzed while the sample tube remains coupled into the sampling system. Finally, it is yet another feature of the invention to permits cleaning, sampling, and desorption of the sample tubes without removing the sample tubes from the system, while still permitting easy replacement of one or more tubes as required.

These and other features and advantages of this invention will be readily apparent to those skilled in the art.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

DETAILED DESCRIPTION OF A PREFERRED EMBODIMENT

Figure 1:
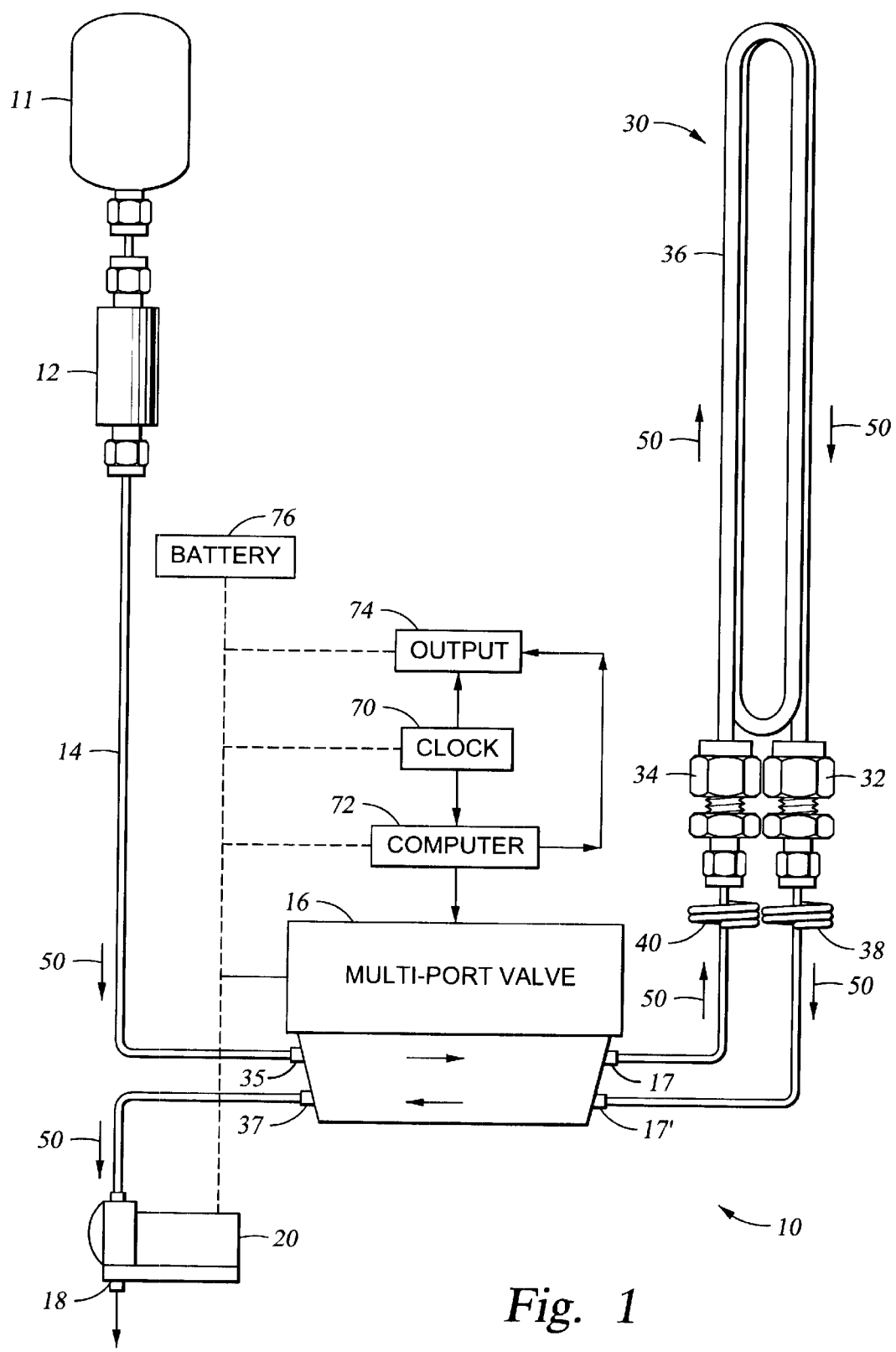
FIG. 1 is a functional block diagram of the AMTAS flow path and associated apparatus.

FIG. 1 illustrates the AMTAS sample collection flow and several components of a sampling system 10 of the invention. The AMTAS employs a multi-port valve 16 which comprises a primary inlet port 35 and primary outlet port 37, and additional ports connecting 16 sorbent tubes 30. The valve 16 is the same general type as a 16-port valve, type MW, manufactured by Valco Instruments Co., Houston, Tex.

Each sorbent tube 30 is connected to the multi-port valve 16 through pairs of the valve ports 17 and 17' and unions 32 and 34. The multi-port valve 16 is constructed and operated in a predetermined sequence to create a flow path through the multi-port valve and only a single connected sorbent tube 30 at a given time and for a given time interval. Gas sample flows from a sample source 11, such as air from a spacecraft cabin, through an inlet filter 12 and intake line 14, into the primary inlet port 35 of the multi-port valve 16, through the multi-port valve, through the sequentially connected sorbent tube 30, back through the multi-port valve and out through a primary outlet port 37, through a pump 20, and then through a pump exhaust 18. The action of the pump 20 draws the sample into and through the connected sorbent tube 30. The gas flow path is shown conceptually by the arrows 50. AMTAS system 10 preferably fits within a right rectangular solid with dimensions of about 9 inches×10 inches×5 inches.

The sequencing of the multi-port valve 16, and the time at which flow is initiated through a given sorbent tube 30, and the duration of the flow through a given sorbent tube, is controlled by a processor such as a computer 72. The movement of the multi-port valve 16 is controlled by an actuator 60 (FIG. 2), which moves the valve to one of thirty two positions, for example, under the control of the computer 72 and a clock 70. Sixteen of the valve positions discretely align a given sorbent tube 30 in the sample collection geometry as described above. The other sixteen valve positions are intermediate park positions as will be discussed in detail below.

The AMTAS is capable of collecting a predetermined number of archive samples for later analysis, and the computer 72 is programmed prior to deployment of the system to collect the samples at predetermined times and for predetermined intervals. The preprogrammed collection times and intervals can, however, be manually overridden by an operator, such as a spacecraft crew member, to obtain an unscheduled sample. The entire system is powered by a battery pack 76 as illustrated in FIG. 1. Battery power is preferably 21, 9 volt lithium or other secondary batteries which supply sufficient power to collect 16 samples over a six month period.

The sorbent tubes 30 are constructed of silica-lined metal tubing 36 and in multiple loops so that the volume of the tube can be adjusted to accommodate varying amounts of sorbent (not shown) to capture particular contaminants of interest. The sorbent tube 30 can be packed with any number of sorbents to trap a single contaminant (i.e. formaldehyde) or multiple contaminants (i.e. volatile organic compounds). For spacecraft applications, the tubes 30 are typically packed with a multi-sorbent bed comprising a material (i.e. Tenax) for trapping volatile organic compounds and a material zno (i.e. Carboxen 569) for trapping very volatile and polar organic compounds. A typical inside diameter of the tubing 30 is ⅛ inch.

The pump 20, which draws samples into and through the sorbent tubes 30, is operated in a pulsed mode only during sampling to conserve battery power. After a preset sampling time, the computer 72 either switches the multi-port valve 16 to the next sorbent tube, or moves the valve to one of the sixteen park positions. In a park position, the valve is set between ports thereby isolating all sorbent tubes 30 in this position. This provides an energy savings in that the multi-port valve then needs to be turned only a fraction of an inch to align the intake port 17 and the exhaust port 17' for the next sorbent tube when called for by the computer 72. This prevents power drain required to actuate the valve actuator 60 in having to rotate repeatedly to a single designated parking position between sampling intervals, and then returning to the next sorbent tube 30 called for by the computer controlled sample sequence.

During the collection of the samples, the AMTAS cooperates with the clock 70 and an output device 74 to automatically record the time of the initiation and duration of each sample. During operation, the system also logs all other sampling operations including logging error messages should any system malfunction occur. Another important feature of the system is the ability to monitor any unusual event. For example, one sorbent tube may be reserved for contingency purposes. Should a contingency event occur, sliding a mode switch 61 (see FIG. 2) from AUTO to MANUAL and depressing a guarded button automatically rotates the multi-port valve to the specified tube, and starts the pump running for a predetermined time period. The switch 61 cooperates with a circuit board 62 of the computer 72

Figure 2:
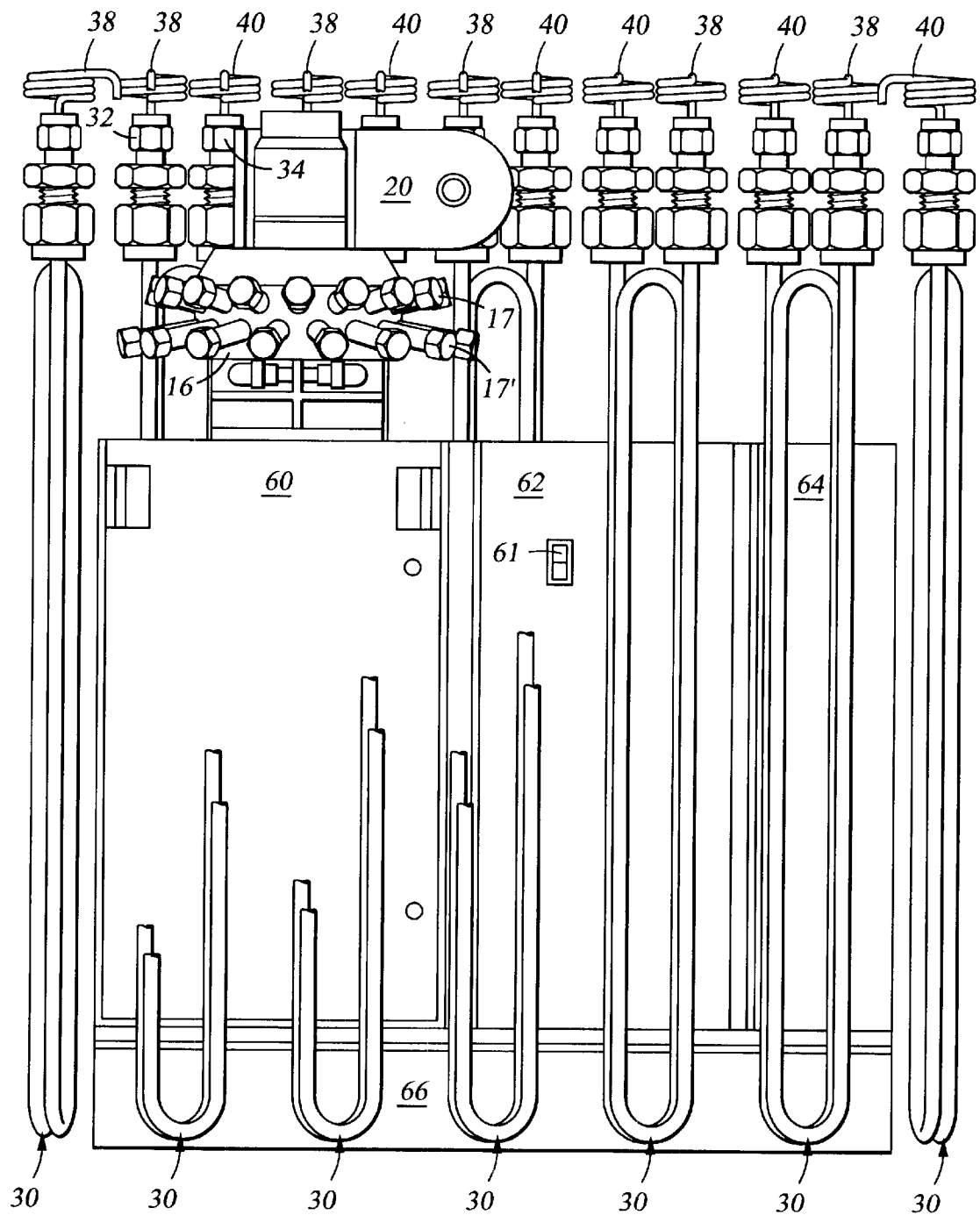
FIG. 2 is a side view of the system showing multiple sorbent tubes, the pump, the multi-port valve, actuator and control circuit boards.
Figure 3:
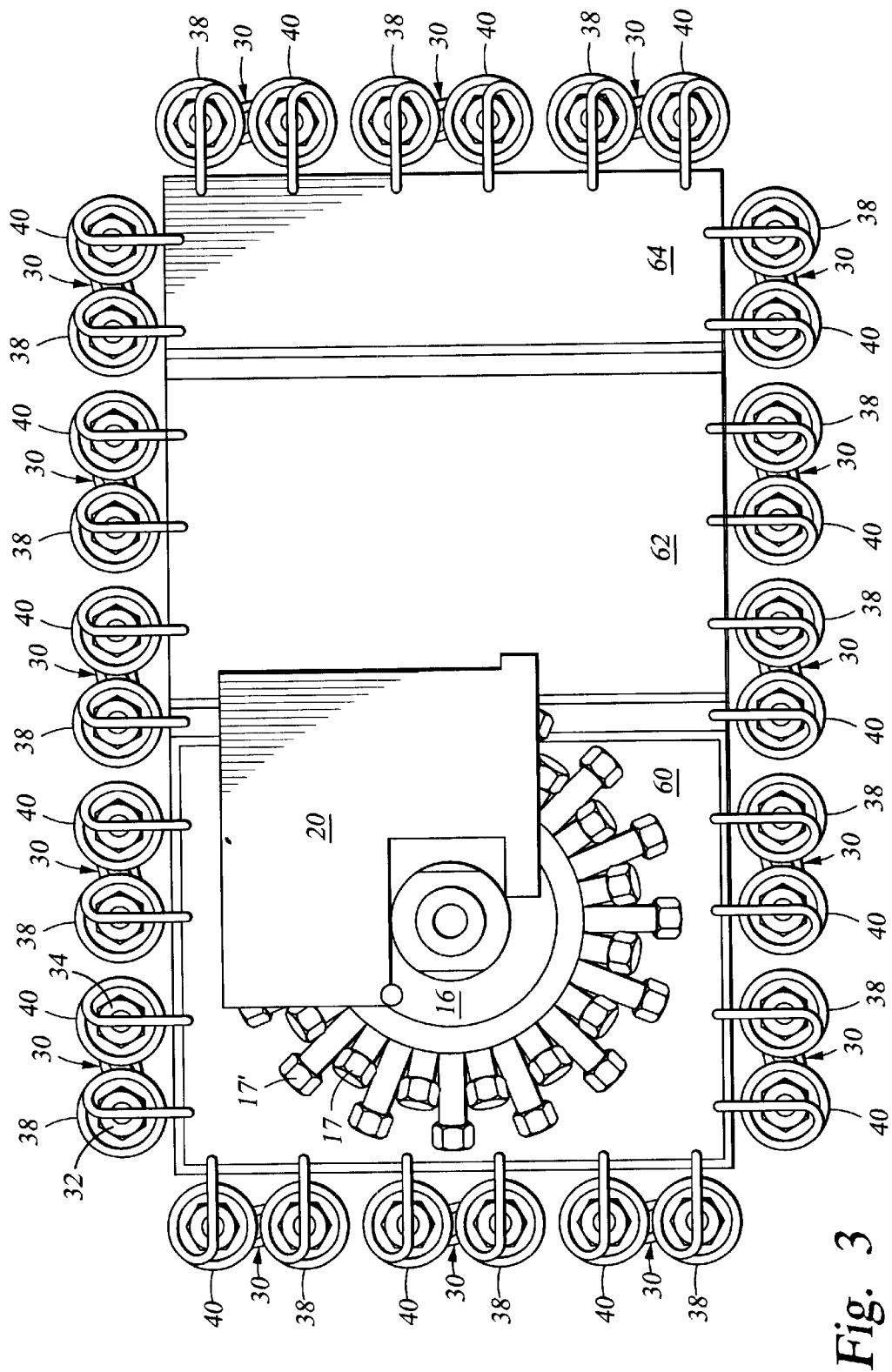
FIG. 3 is a top view of the system showing multiple sorbent tubes, the pump, the multi-port valve, actuator and control circuit boards.

FIGS. 2 and 3 are in proportional scale illustrating the preferred physical layout of the AMTAS. FIG. 2 is a side view of the system showing multiple sorbent tubes 30. the pump 20, the multi-port valve 16, the actuator 60 and control circuit boards 62, 64 and 66 of the computer 72 and clock 70. FIG. 3 is a top view of the system illustrating the same components. It should be noted that the pump 20, the multi-port valve 16, and the sorbent tubes are all in close physical proximity to minimize the volume encompassed within them to minimize the volume of gas that must be pumped by the pump 20 to take a sample.

Figure 4:
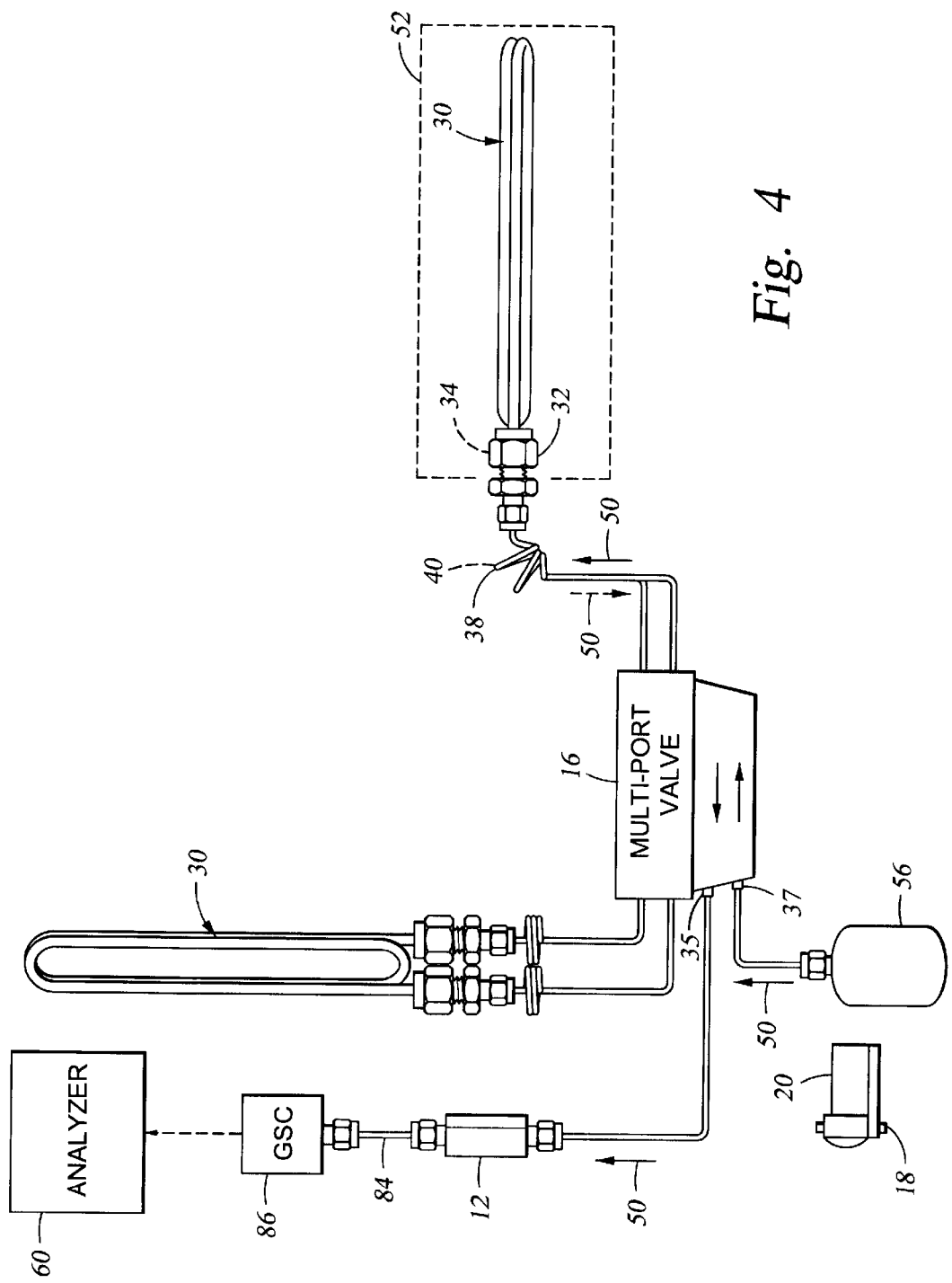
FIG. 4 shows a sorbent tube position for sample retrieval.

FIG. 4 illustrates sample retrieval and processing steps of the invention. FIG. 4 assumes that a sample has been captured by a representative sorbent tube 30, and the sorbent within the tube has absorbed a sample of a trace element of interest. This technique of capturing a test sample is referred to herein as the gas carrier method. Also in the gas carrier method, the sorbent is heated to release the absorbed trace constituents and this sample is then carried by an inert gas, such as nitrogen, from the system for capture and/or analysis.

Once the AMTAS is returned to a facility for analysis, the pump 20 is disconnected from the multi-port valve 16 at the primary outlet port 37, and a source 56 of pure nitrogen is connected to this port. Each sorbent tube 30, as it is selected for desorption, is released from a clamp (not shown) and bent downward approximately ninety degrees by means of coil spring fittings 38 and 40, and placed into a desorption heater 52 illustrated conceptually with broken lines. It should be noted that the selected sorbent tube is positioned for desorption without removing the tube from the AMTAS. Other tubes are unaffected during this process.

Meantime, a clean, proofed, evacuated gas sample container 86 (GSC) is attached to the sample inlet filter 12 by means of a suitable flow line 84. Nitrogen is flowed at preferably 10 cc/minute from the source 56 through the port 37 of the multi-port valve 16 and through the sorbent tube 30 being heated, back through the multi-port valve 16 and inlet fitting 35 and into the GSC 86. Gas flow is again conceptually illustrated with the arrows 50.

After the heating step, the sorbent tube 30 is quickly removed from the heater 52 and cooled for about 3 minutes by means of a fan, the multi-port valve 16 is closed to isolate the GSC 86, and the GSC is removed from the system for analysis by an analyzer 60, such as a gas chromatograph/mass spectrometer. Alternately, desorbing directly into the analyzer 60 is possible, but allows only one opportunity for analysis and prevents archiving of the sample.

After removing the sorbent sample using the carrier gas method, each sorbent tube is heated preferably at about 280° Centigrade with the heater to purify the sorbent for use in the next sampling sequence. Once proofed, it is dosed with 20 cc of a three component surrogate standard. It is unnecessary, therefore, to disassembly to AMTAS for cleaning prior to repeated usage.

In alternate embodiments, the AMTAS can be loaded with a variety of different sorbents that permit the sampling and analysis of a number of specific reactive compounds. In fact, the AMTAS compound sampling range can be significantly enhanced by the careful selection of a variety of sorbents, and the control of the amount of sorbent material used by the dimensions of the sorbent tubes 30. It is also possible to "piggyback" several AMTAS units together to increase the number of sample tubes but using only a single controller component. This arrangement yields a very small, low power, portable device adaptable for use in many situations.

The principles, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

I claim:

1. A system for capturing samples of trace constituents of ambient air comprising:
   a. a source of ambient air from which samples are to be taken;
   b. a multi-port valve coupled to the source;
   c. plurality of sorbent tubes coupled to the multi-port valve, each of the sorbent tubes containing a sorbent inside the tube;
   d. a pump to sequentially draw air from the source through one of the sorbent tubes at a time as directed by the multi-port valve; and
   e. an actuator coupled to the multi-port valve to move the multi-port valve between a first position and a second position, wherein in one of the first position and the second position, the valve is set between ports isolating all sorbent tubes.

2. The system of claim 1, wherein the multi-port valve includes a plurality of inlet ports and a plurality of outlet ports and each of the plurality of sorbent tubes is coupled to one of the inlet ports and one of the outlet ports of the multi-port valve.

3. The system of claim 2, wherein each of the sorbent tubes forms a loop.

4. The system of claim 3, further comprising a dedicated inlet spring coil tubing coupling each sorbent tube to the inlet port and a dedicated outlet spring coil tubing coupling each sorbent tube to the outlet port.

5. The system of claim 3, wherein in the first position the multi-port valve defines a flow path through a sorbent tube and in the second position the multi-port valve is in a park position in which no flow path is directed through any of the sorbent tubes.

6. The system of claim 5, wherein the movement of the multi-port valve is controlled by the computer at predetermined times, intervals, and durations.

7. The system of claim 5, wherein the pump is controlled by the computer.

8. The system of claim 5, further comprising an output device coupled to the computer for logging predetermined events.

9. The system of claim 3, wherein in the first position the multi-port valve is in a park position in which no flow path is directed through any of the sorbent tubes and in the second position the multi-port valve defines a flow path through a sorbent tube.

10. The system of claim 3, further comprising a computer coupled to the actuator to control the movement of the multi-port valve.

11. The system of claim 1, wherein one of the sorbent tubes contains a sorbent that is different than another of the sorbent tubes.

12. The system of claim 1, wherein the sorbent tubes are lined on an inside surface with glass.

13. A method of capturing a sample of a trace element form ambient air comprising the step of:
    a. connecting a source of ambient air into an inlet port of a multi-port valve;
    b. connecting a plurality of sorbent tubes to the multi-port valve, each of the sorbent tubes containing a sorbent to absorb a trace element from ambient air;
    c. connecting a pump to an outlet port of the multi-port valve;
    d. orienting the multi-port valve to direct a flow path through a selected one of the plurality of sorbent tubes;
    e. activating the pump to draw a quantity of ambient air through the selected sorbent tube; and
    f. orienting the multi-port valve so the valve is set between ports.

14. The method of claim 13, further comprising the step of then orienting the multi-port valve to isolate a sample in the selected sorbent tube.

15. The method of claim 14, wherein the steps of orienting the multi-port valve to direct a flow path through a selected one of the plurality of sorbent tubes and then orienting the multi-port valve to isolate a sample in the selected sorbent tube is controlled by a computer.

16. The method of claim 13, further comprising the steps of:
    a. disconnecting the source of ambient air from the inlet port of the multi-port valve;
    b. disconnecting the pump from the outlet port of the multi-port valve;
    c. connecting an analyzer to the inlet port of the multi-port valve;
    d. connecting a source of an inert gas to the outlet port of the multi-port valve;
    e. heating a sorbent tube to cause the sorbent within the tube to release the trace element absorbed by the sorbent; and
    f. directing flow of inert gas from the source of an inert gas through the sorbent tube and the multipart valve into the analyzer.

17. A system for capturing samples of trace constituents of ambient air comprising:
   a. a source of ambient air from which samples are to be taken;
   b. a multi-port valve coupled to the source;
   c. a plurality of sorbent tubes coupled to the multi-port valve, each of the sorbent tubes containing a sorbent inside the tube; and
   d. a pump to sequentially draw air from the source through one of the sorbent tubes at a time as directed by the multi-port valve, wherein the multi-port valve includes a plurality of inlet ports and a plurality of outlet ports and each of the plurality of sorbent tubes is coupled to one of the inlet ports and one of the outlet ports of the multi-port valve and wherein each of the sorbent tubes forms a loop.

18. The system of claim 17, further comprising a dedicated inlet spring coil tubing coupling each sorbent tube to the inlet port and a dedicated outlet spring outlet spring coil tubing coupling each sorbent tube to the outlet port.

19. The system of claim 17, wherein in the first position, the multi-port valve defines a flow path through a sorbent tube and in the second position, the multi-port valve is in a park position in which no flow path is directed through any of the sorbent tubes.

20. The system of claim 19, wherein the movement of the multi-port valve is controlled by the computer at predetermined times, intervals, and durations.

21. The system of claim 19, wherein the pump is controlled by the computer.

22. The system of claim 19, further comprising an output device coupled to the computer for logging predetermined events.

23. The system of claim 17, wherein in the first position, the multi-port valve is in a park position in which no flow path is directed through any of the sorbent tubes and in the second position, the multi-port valve defines a flow path through a sorbent tube.

24. The system of claim 17, further comprising a computer coupled to the actuator to control the movement of the multi-port valve.

* * * * *

UNITED STATES PATENT AND TRADEMARK OFFICE
CERTIFICATE OF CORRECTION

PATENT NO.    : 6,477,906 B1
DATED         : November 12, 2002
INVENTOR(S)   : Roger Peterson It is certified that error appears in the above-identified patent and that said Letters Patent is hereby corrected as shown below:

Column 2,
Line 29, please change "form" to -- from --.
Line 67, please change "multipart" to -- mulitport. --

Column 9,
Line 20, please change "outlet spring outlet spring" to -- outlet spring --.

Signed and Sealed this

Fourth Day of March, 2003

JAMES E. ROGAN
*Director of the United States Patent and Trademark Office*